(12) United States Patent
Fuller et al.

(10) Patent No.: US 8,329,246 B2
(45) Date of Patent: Dec. 11, 2012

(54) ORIENTED COLLAGEN GEL

(75) Inventors: Gerald G. Fuller, Stanford, CA (US); John E. Kirkwood, Santa Clara, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 442 days.

(21) Appl. No.: 12/660,702

(22) Filed: Mar. 2, 2010

(65) Prior Publication Data

US 2010/0227043 A1    Sep. 9, 2010

Related U.S. Application Data

(60) Provisional application No. 61/209,239, filed on Mar. 4, 2009.

(51) Int. Cl.
*A61L 33/14* (2006.01)
(52) U.S. Cl. ...... 427/2.24; 623/917; 435/395; 514/17.2; 514/18.6
(58) Field of Classification Search .......... 427/2.24; 623/917; 435/395; 514/17.2, 18.6
See application file for complete search history.

(56) References Cited

U.S. PATENT DOCUMENTS
2010/0227043 A1* 9/2010 Fuller et al. ............... 427/2.24

FOREIGN PATENT DOCUMENTS
WO  WO/2007/038601  4/2007
WO  WO/2009/064437  5/2009

OTHER PUBLICATIONS

Lanfer et al. (2008) Aligned fibrillar collagen matrices obtained by shear flow deposition. Biomaterials. Oct. 2008;29(28):3888-95.
Jiang et al. (2004) Assembly of collagen into microribbons: effects of pH and electrolytes. Journal of Structural Biology 148 (2004) 268-278.
Physical and Chemical Modifications of Collagen Gels: Impact on Diffusion, Erikson et al., Biopolymers 89(2):135-143, 2007.
Cholesteric Twist of Collagen: In Vivo and In Vitro, Giraud-Guille et al., Mol. Cryst. Liq. Cryst. 153:15-30, 1987.
Comparison of epoxides on grafting collagen to polyurethane and their effects on cellular growth, Huang et al., *Journal Biomedical Materials Research*, 39: 630-636, 1998.
Microfluidic alignment of collagn fibers for in vitro cell culture, Lee et al., Biomed. Microdevices 8:35-41, 2006.
Schwann cell behavior in three-dimensional collagen gels: Evidence for differential mechano-transduction and the influence of TGF-beta 1 in morphological polarization and differentiation, Rosner et al., Exp. Neurol. 195:81-91, 2005.

* cited by examiner

*Primary Examiner* — Timothy Vanoy
(74) *Attorney, Agent, or Firm* — Lumen Patent Firm

(57) ABSTRACT

Techniques for the production of flow-oriented collagen gels using hydrodynamics to influence the assembly of collagen fibers. Highly concentrated monomeric solutions of collagen are subjected to shear and extensional flow as they are drawn onto a substrate to induce fibrillogenesis under a high Ph buffer. The produced gel captures the flow induced ordering of molecular collagen upon fibril formation. The depositing or the induction of fibrillogenosis occurs without the application of a magnetic field to the concentration of collagen. These highly oriented 3D scaffolds are capable inducing contact guidance and guiding mammalian cell growth. The collagen fibers mimic the construction of in vivo fibers with the characteristic D-periodicity and the integrin receptors on the fibroblasts respond to this organization. The industrial applications of three-dimensional collagen gels as a biomaterial are widespread from drug delivery to burn repair or tissue engineering system.

20 Claims, 13 Drawing Sheets

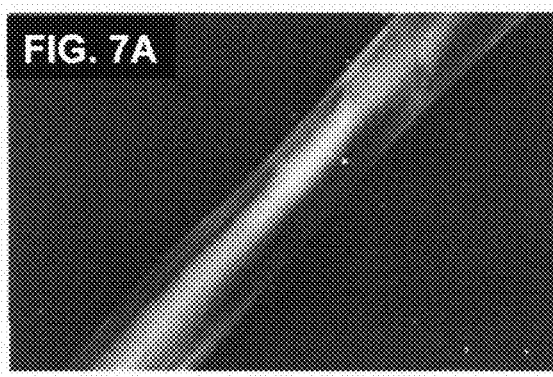
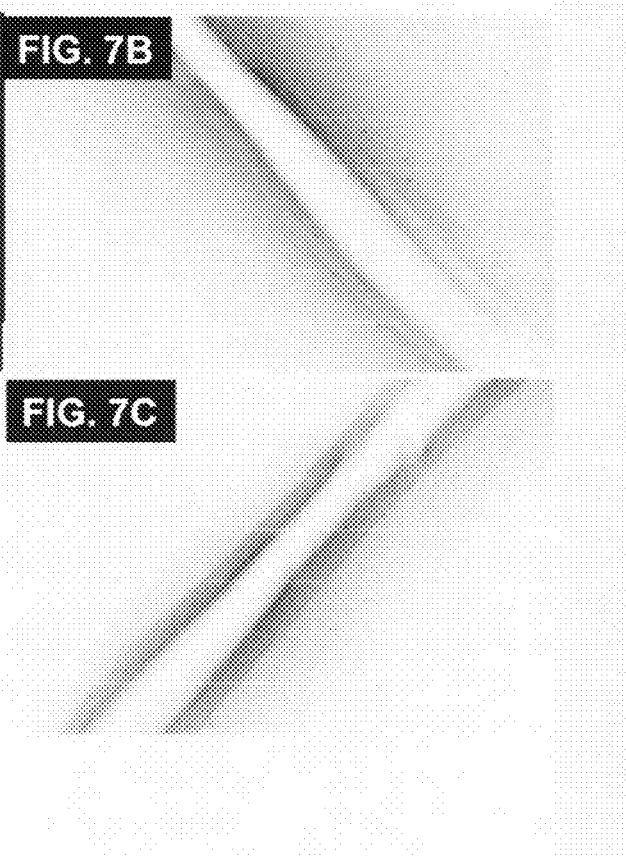
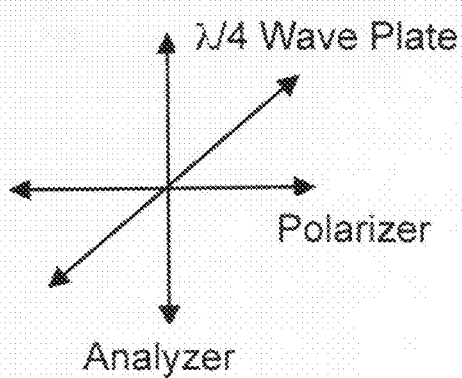

ORIENTED COLLAGEN GEL

CROSS-REFERENCE TO RELATED APPLICATIONS

This application claims priority from U.S. Provisional Patent Application 61/209,239 filed Mar. 4, 2009, which is incorporated herein by reference.

FIELD OF THE INVENTION

The invention relates to collagen gels and method of using these gels. In particular, the invention relates to oriented collagen gels for cell growth, drug delivery or tissue engineering.

BACKGROUND OF THE INVENTION

Collagen gel structures have many benefits as a drug delivery and tissue engineering system. They have been used for many years in plastic surgery as an injectable implant because they are visco-elastic and can flow under stress. However, the downside of collagen gels is the high pore size (tens of nanometers), which makes controlled release difficult without attaching the molecule to collagen. Randomly oriented gels are also too weak to bear tensile loads or for surgical manipulation. In addition, while the mechanical properties of collagen gels can be either altered by covalent or non-covalent cross-linking (heat, chemicals, or UV irradiation) or combined with other composites to increase strength. The effect of these techniques are not straight forward, and some can lead to the degradation of collagen or have an adverse cytotoxicity on cell growth.

Unoriented collagen gels have been produced as cell culture substrate for almost fifty years. They can be produced by warming a neutralized solution of collagen to physiological temperature. One method for creating an oriented collagen gel is the use of a high strength magnetic field to induce the orientation of the collagen fibers during fibrillogenesis. This method requires the use of a strong magnetic field, 0.5-5 Tesla depending on gel dimensions, making it impractical for commercial production. Oriented collagen gels were produced in a microfluidic channel. In this method, a solution of alkaline collagen was allowed to polymerize in PDMS channels 10-400 microns in width. The fluids were briefly subjected to a flow velocity of 5-10 mm/s as they entered the channel with a stationary depositing device. The flow rates in this example, were not significant enough to manipulate the orientation of the collagen molecules. The invention provides new techniques to create oriented collagen gels.

SUMMARY OF THE INVENTION

The present invention provides techniques for the production of flow-oriented collagen gels using hydrodynamics to influence the assembly of collagen fibers. Highly concentrated monomeric solutions of collagen are subjected to shear and extensional flow as they are drawn onto a substrate to induce fibrillogenesis under a high Ph buffer. The produced gel captures the flow induced ordering of molecular collagen upon fibril formation. The depositing or the induction of fibrillogenosis occurs without the application of a magnetic field to the concentration of collagen.

These highly oriented 3D scaffolds are capable inducing contact guidance and guiding mammalian cell growth. The collagen fibers mimic the construction of in vivo fibers with the characteristic D-periodicity and the integrin receptors on the fibroblasts respond to this organization. The industrial applications of three-dimensional collagen gels as a biomaterial are widespread from drug delivery to burn repair or tissue engineering system.

In one embodiment, a method of making an oriented collagen gel is provided. A concentration of collagen is deposited onto a substrate by a depositing device to induce fibrillogenesis while under a pH buffer of at least 5 or at least 7, and under a physiological temperature. In one example, the substrate contains a coating of collagen prior to the depositing step. The concentration of collagen could be at least 3 mg/ml, is at least 5 mg/ml, is at least 10 mg/ml, is at least 20 mg/ml or is at least 40 mg/ml. Changes in concentration results in e.g. controlling the porosity of the collagen gel.

The depositing device has a depositing speed (e.g. of at least 100 mm/s) during the deposition and the concentration of collagen has a travelling speed (e.g. of at least 0.3 mL/min) while being deposited. The depositing speed and travelling speed are both larger than zero, but move in opposite direction from each other, which is important to impose both a shear and extensional force component to the concentration of collagen during deposition. In one aspect, the deposition of the collagen concentration is defined by a draw ratio of the depositing speed and travelling speed. The draw ratio should be larger than 0, or could be at least 1, at least 2, at least 3 or at least 4. The length of the collagen fibers could be about 1 micrometer or more, 10 micrometer or more, or 100 micrometer or more, and have a D-periodicity of 67 nm or about 67 nm. The orientation of collagen gel fibers could be further increased by pulling or stretching the oriented collagen gel.

BRIEF DESCRIPTION OF THE DRAWINGS

FIGS. 7A-C shows according to an embodiment of the present invention oriented collagen gel observed between (7A) crossed polarizers, and (7B & 7C) with a quarter wave plate inserted into the optical train at 45° to polarizer. The orientation of the polarizer, analyzer and wave plate with respect to sample direction is shown. The color of the gel changes when rotated with respect to the orientation of the quarter wave plate. (2× Magnification)

DETAILED DESCRIPTION

Figure 1:
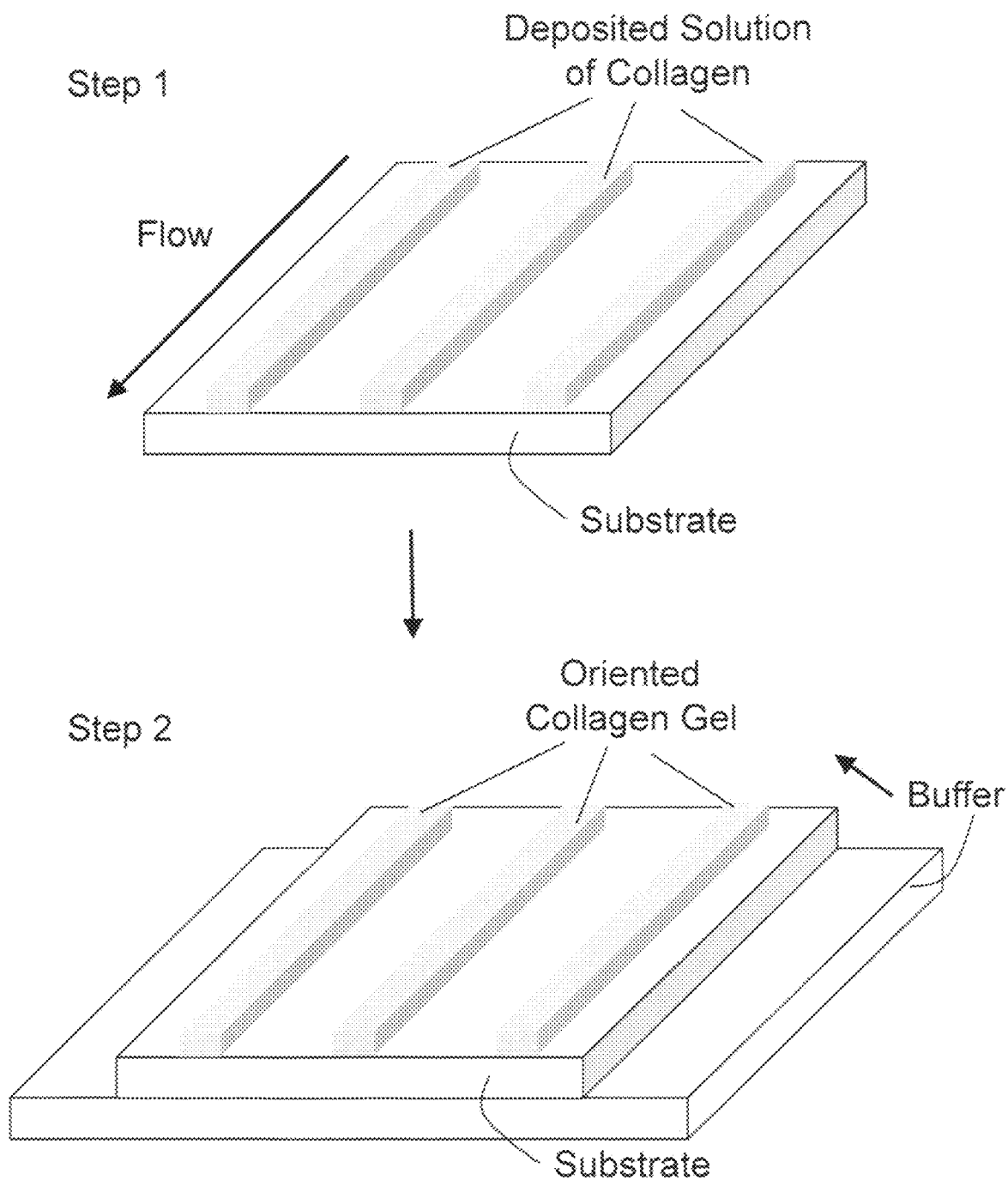
FIG. 1 shows according to an embodiment of the invention a method to produce oriented collagen gels through submersion under buffer. Step 1: Robotic deposition of highly concentrated collagen solution onto glass substrate. Step 2: Substrate is moved to a high pH buffer, inducing the fibrillogenesis of the collagen solution.

The description presents the production of flow-oriented collagen gels using hydrodynamics to influence the assembly of collagen fibers. Highly concentrated (monomeric) solutions of collagen are deposited on a substrate and subsequently induce fibrillogenesis under a high pH buffer. During the deposition the collagen solution is subjected to shear and extensional flow as they are drawn onto a substrate. The produced gel captures the flow induced ordering of molecular collagen upon fibril formation. The oriented collagen fibers are observed using optical birefringence measurements and the culture of adult human fibroblasts. The growth and polarization of adult human fibroblasts on these oriented gels is discussed.

Materials

Rat Tail Collagen, Type I (BD Biosciences) was purchased at stock concentrations of 3.6 mg/mL and 10 mg/mL in 0.02 N Acetic Acid (pH~3.5). The 10 mg/mL solution was then dialyzed against polyethylene glycol (Fluka) for 20 minutes at 4° C. until the solution reached a final concentration of approximately 20 mg/ml.

Silica glass was cleaned by plasma treatment using a plasma cleaner (Gala Instrumente, Prep 5) on 50% power for 5 minutes. Some experiments were conducted with a thin coating of collagen (concentration <0.1 mg/mL) dried onto the glass as an aid to adhesion of the collagen gels to the substrate.

The buffer used to induce fibrillogenesis of collagen molecules was 10× phosphate buffered saline, PBS, (Gibco, Invitrogen Corporation). The buffer has a molarity of 0.1 and pH of 7.2. The components of 10×PBS are 2100 mg/L of potassium phosphate monobasic (KH2PO4), 90,000 mg/L sodium chloride (NaCl), and 7260 mg/L sodium phosphate dibasic (Na2HPO4-7H2O). The PBS was heated to 37° before use.

Methods

The collagen gel was prepared for imaging with the atomic force microscope by exchanging the PBS buffer with deionized water (Milli-Q). The exchange was performed a minimum of three times to remove salt residue. The films were allowed to dry overnight in a vacuum desiccator. Atomic force microscopy was performed on the collagen films using a Veeco Multimode AFM in tapping mode using Tap300A1 tips (Budget Sensors Tap300A1) with nominal force constant of 40 mN/m and resonant frequency of 300 kHz.

Human fibroblasts (ATCC CRL-2091) were cultured on the substrates in DMEM media supplemented with 0.1% FBS, 0.01% 100× penicillin/streptavidin, 0.01% 100× glutamine, 0.01% MEM Non-Essential Amino Acids, and 0.01% 100× Sodium pyruvate. Cells were plated at a density of approximately 10,000 cells/ml and grown for 12-48 hours at 37° C. with 5% CO2. The cells were fixed in a solution of 10% formaldehyde in 1× phosphate buffered saline (PBS) for 10 minutes. Images were captured with a 10× phase contrast objective using a Nikon TE300 microscope.

For fluorescent imaging of the cellular actin fibers, the cells were stained with Alex Fluor 488 Phalloidin (Invitrogen). The staining protocol is as follows. The growth media is aspirated and the plates are washed one time in PBS and fixed with 3% Formaldyhde in PBS for 10 minutes. The cells are permeabilized with a solution of 1% Triton in PBS for 10 minutes. The plates are then washed twice with a solution of 0.1% Triton in PBS. Blocking buffer composed of 5% horse serum and 0.1% Triton in 1×PBS is then added to the plates for 20 minutes. The fluorescent dye is dispersed in blocking buffer and set on the plates for 1 hour. The plates are washed three times in a 0.1% Triton in PBS solution, mounted with Vectashield (Vector Laboratories) and a glass slide, and stored in the dark at −20° C. until use. Fluorescent dyes were excited with a Mercury lamp on a Nikon Microphot and Pentamax cooled CCD camera and images recorded with Metamorph Software. Pseudo-coloring of fluorescent images was done using Adobe Photoshop.

Collagen Submersion at High pH

Substrates for these experiments were created following a two step procedure. In the first step, deposition of collagen stripes onto glass substrates was performed following the procedure outlined in the APPENDIX infra. Immediately after the deposition of the collagen was complete the glass substrate was placed into a bath of 10×PBS at 37° C., Step 2. A schematic of this procedure is shown in FIG. 1.

The solution of highly concentrated collagen is in a fluid state upon entering the buffer. The timeframe for the robotic deposition in Step 1 is approximately 1 minute while the gelation time of Step 2 is an order of magnitude greater. We observed that the fibrillogenesis of the collagen solution begins immediately upon entry into the buffer. This is monitored visually as the translucent collagen film becomes an opaque collagen gel. The substrates were kept under the buffer for at least 1 hour before removal.

Deposition Under High pH

Figure 2:
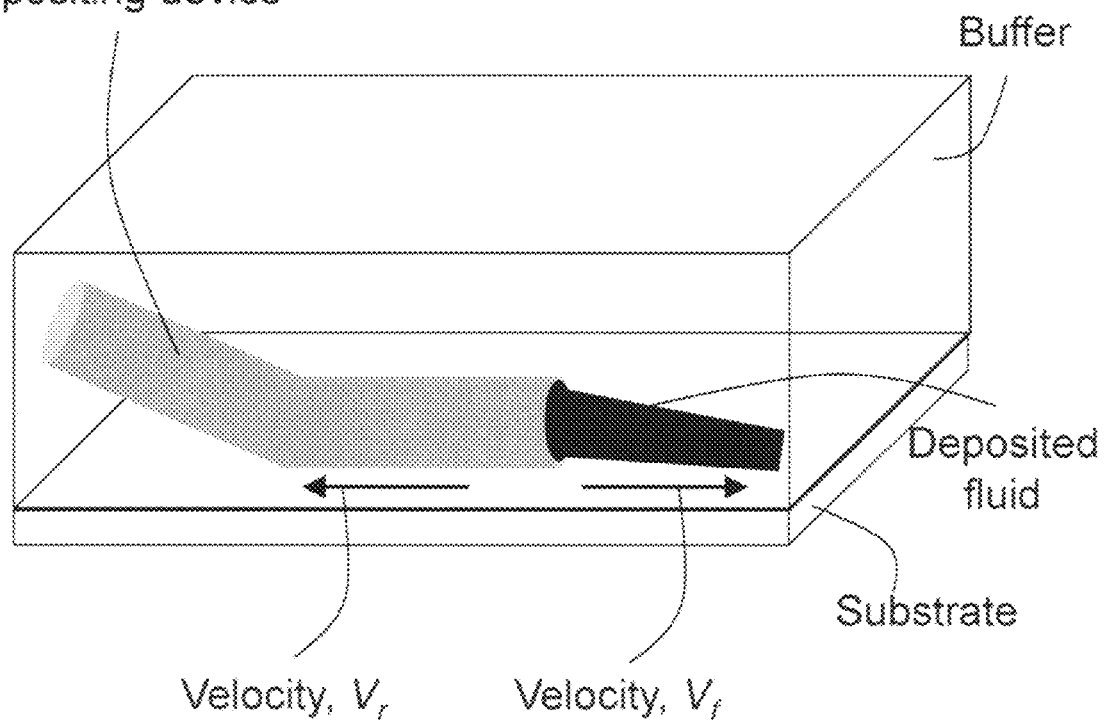
FIG. 2 shows according to an embodiment of the present invention a schematic of robotic deposition under high pH environment. Fluid is drawn onto substrate with fluid and syringe tip velocity in opposing directions.

In this experiment, solutions of collagen were deposited under flow from an acid solubilized state into a high pH environment. The collagen monomers were aligned by strong hydrodynamic flow exiting a syringe needle. Further alignment of the collagen molecules was achieved by ejecting fluid from the needle while simultaneously moving the syringe in the opposite direction (FIG. 2).

Immediately upon entry into the buffer, the acidic solution began to solidify into a gelled structure. This was confirmed visually with the formation of an opaque gel with elevated elastic moduli. The procedure was performed manually at a high rate of speed to maximize the flow-induced orientation of the molecules. The solution of collagen was deposited from a 1 mL syringe and needle either directly on top of the silica glass substrate, onto the surface of a plastic tissue culture dish, or allowed to float freely in the buffer. Different substrates were used to probe the adhesion of the collagen gel onto the substrate to provide an extensional component to the flow as the solution was drawn away from the starting point. The samples were cured for 1 hour in 10×PBS before removal. The collagen gels produced without a substrate were removed from the buffer and placed on a glass slide using tweezers. Syringe needle selection of 20-26 gauge enabled the production of collagen gels of varying size. Three different concentrations of collagen were used 3.7, 8.6, and 24 mg/mL.

Ordered Gel Production Using PBS Submersion

The same methodology as described in APPENDIX infra was followed, but have replaced the ambient desiccation of the collagen film with rapid fibrillogenesis in a high pH solution. The formation of collagen fibers stabilizes the molecular order imparted by the hydrodynamic flow during deposition.

Figure 3:
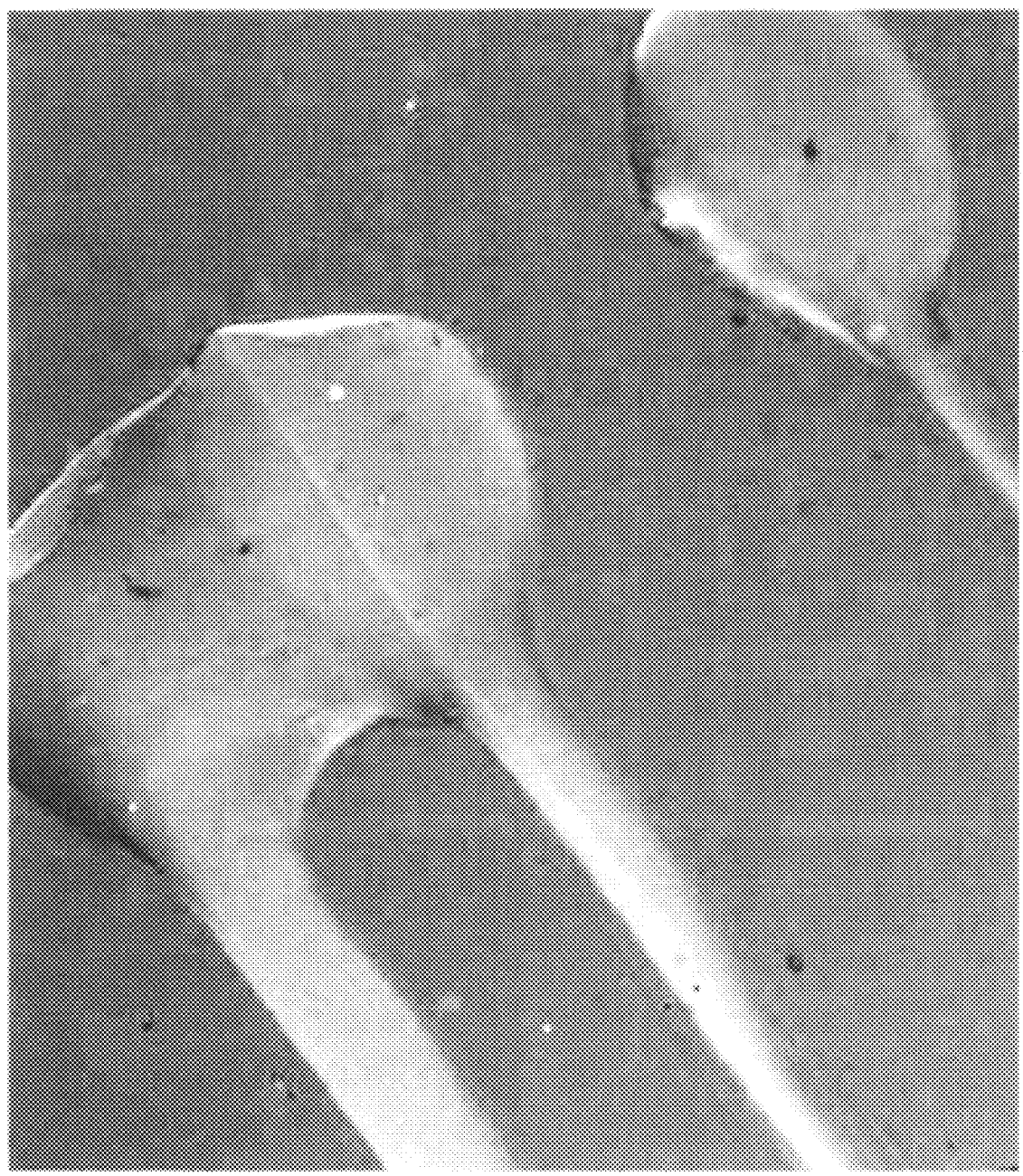
FIG. 3 shows according to an embodiment the present invention the deposition of highly concentrated collagen solution onto glass followed by submersion into 10×PBS buffer. Sample is shown between crossed polarizers in light microscope at 4× magnification.

The fibrillogenesis was not quantitatively tracked but can be inferred from the visual increase in turbidity of the deposited collagen solution from a translucent material to an opaque gel. This rapid phase transition occurred in less than one minute. The amount of material deposited onto the glass slide varies with the parameters of each deposition (flow rate, robot speed). In a typical deposition, where a robot velocity of 100 mm/s and flow rate of 0.3 mL/min the amount of material deposited per stripe is a couple of microliters. These thin stripes of highly concentrated collagen form cholesteric liquid crystal films when allowed to dry in the air. However, when these solutions are moved to a high pH buffer before drying they form oriented collagen gels. In FIG. 3 we show three gels between crossed polarizers. The gels are highly birefringent and retain the shape of the robot deposition pattern. The round shape at the top of the gel is the start of the robotic deposition. As the robotic arm moves away from this point, it leaves a thin band of collagen. The birefringence is uniform for the length of the gel and extinction of the signal is achieved by sample rotation of 45°. This suggests that the submersion of the solution after deposition is quicker than the relaxation of the fluid, and that the fluid is oriented upon deposition.

Figure 4:
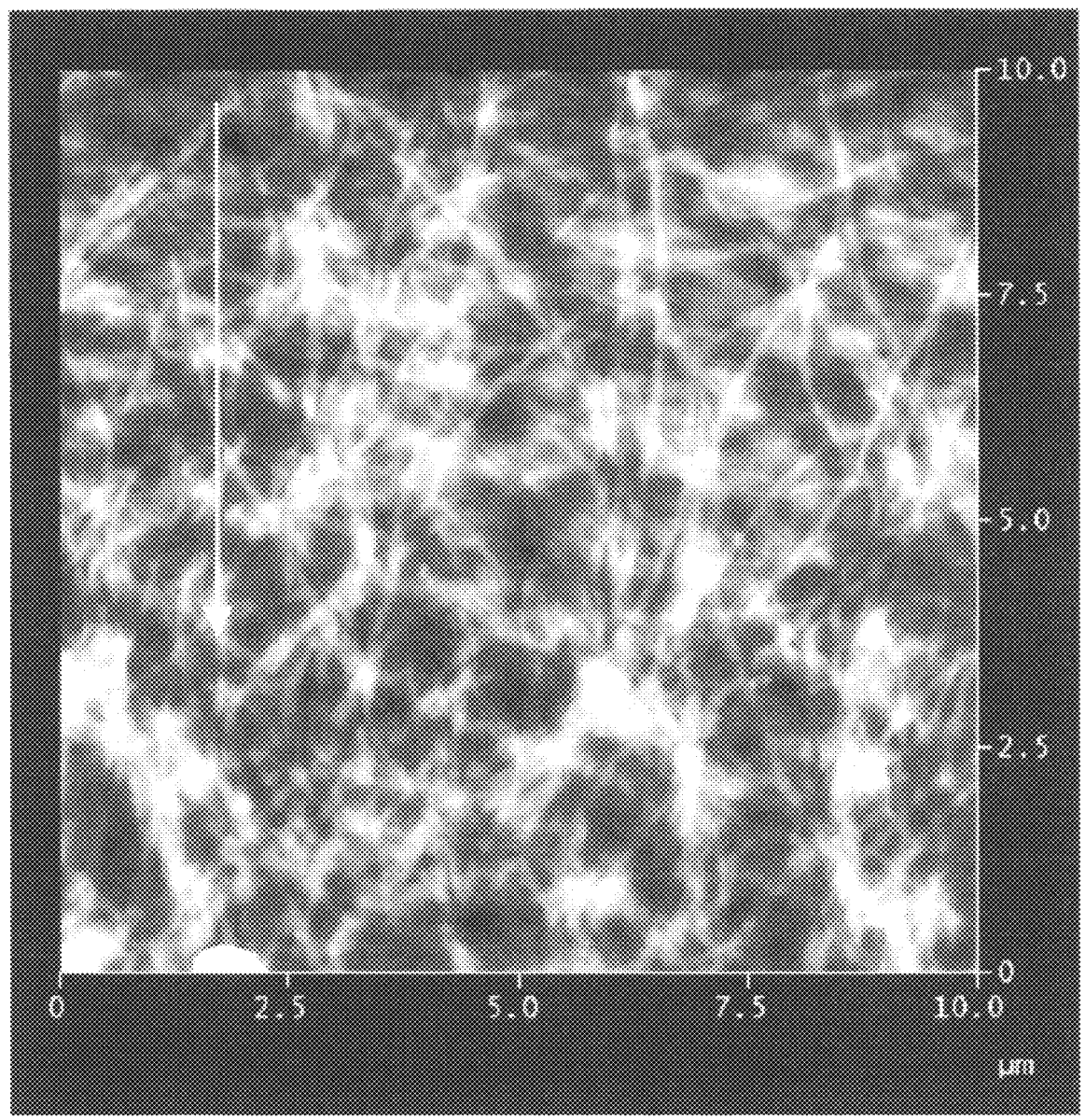
FIG. 4 shows according to an embodiment of the present invention AFM height mode image of dehydrated collagen gel displaying long fibrils oriented in the direction of flow deposition (Arrow). Gel is formed by submersion in warm 10×PBS immediately following robotic deposition on glass. 10 µm×10 µm image, 150 nm height scale.

The collagen gel structure is well hydrated. The mechanical properties are weak and the gel can be torn easily with light pressure. These properties make the gel difficult to handle off of the substrate and to image properly with either the AFM or SEM. To image the gel, the water was removed resulting in a structural collapse of the gel. We did not expect the loss of water to induce a change in fiber length or diameter, making it possible to analyze the composition of collagen but not the density or porosity of the gel network. Images of the collagen gel taken with the atomic force microscope are shown in FIG. 4 and confirm that the gel is constructed of long collagen fibers. The collagen fibers appear tens of microns in length with a range of widths of ~100 nm. These collagen fibers possess the characteristic 67 nm D-periodicity of fibers formed under high pH conditions.

Growth of Adult Human Fibroblasts on Oriented Collagen Gels

The adult human fibroblasts used for this study are known to possess the integrin receptors specific to collagen fibers which are crucial for contact guidance. The behavior of the fibroblast cells on the collagen matrix, polarization and extension of the cell body, will provide a picture of the underlying collagen fiber orientation. The growth medium used in the culture of adult human fibroblasts has a neutral pH and the gels are not subjected to the same loss of volume as the dehydration step required for AFM imaging.

Figure 5:
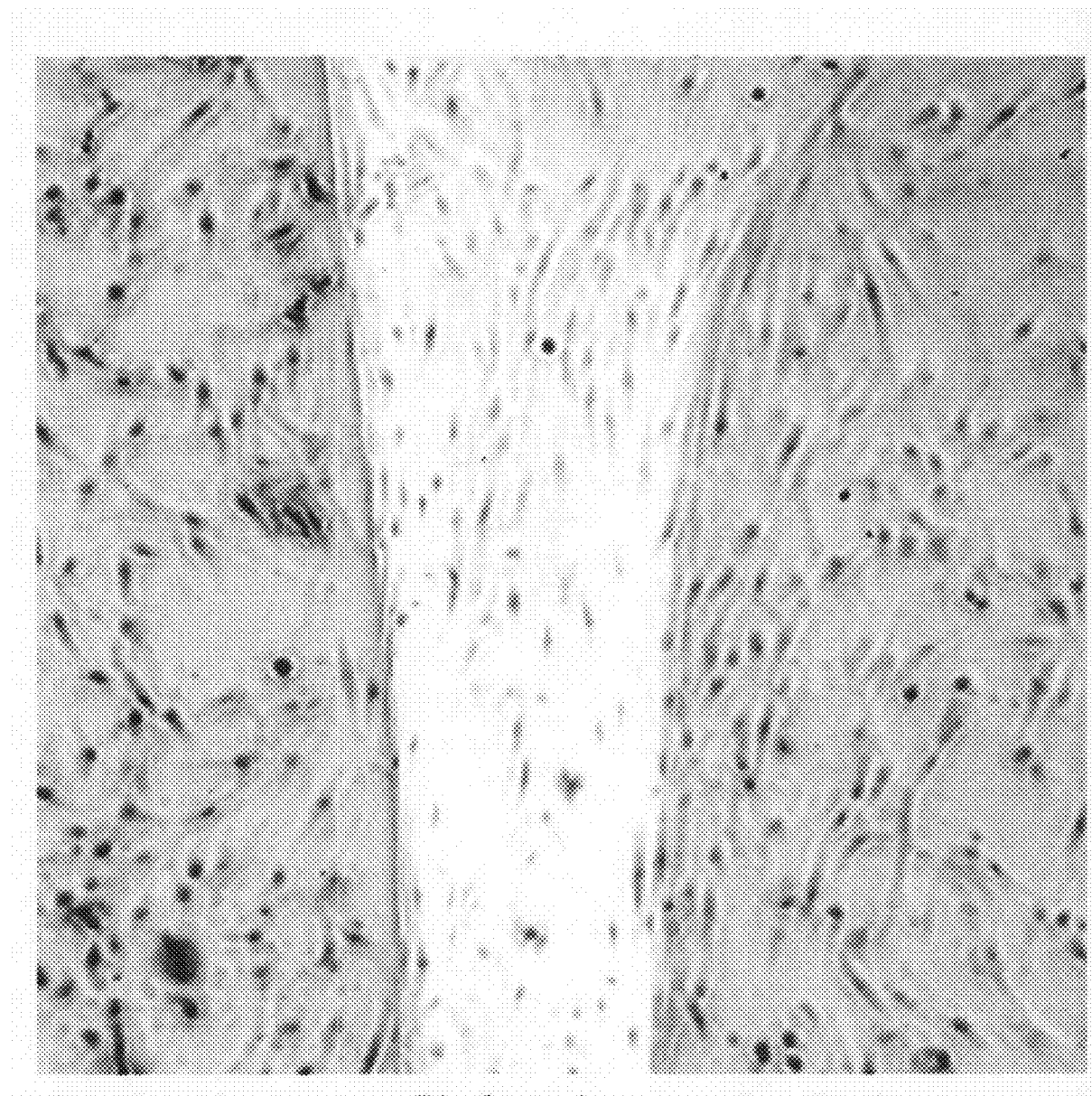
FIG. 5 shows examples according to an embodiment of the present invention collagen gel imaged between crossed polarizers with adult human fibroblasts. Fibroblasts are oriented parallel to the deposition of the collagen, and cell polarization follows the areas of birefringence. Regions outside the gel appear darker because they are not birefringent. The cell growth in the darker area is unoriented.

We observed adult human fibroblasts grown on the collagen gels to orient in the direction of flow deposition. A sample of this fibroblast polarization is given in FIG. 5 where the collagen gel and cells are imaged under crossed polarizers. The fibroblasts are stretched out parallel to the long axis of the gel, the direction of flow deposition. This both confirms the ability of fibroblasts to orient in the direction of collagen fiber alignment and the orientation of the collagen molecules by hydrodynamic flow prior to fibrillogenesis as observed through birefringence.

Figure 6:
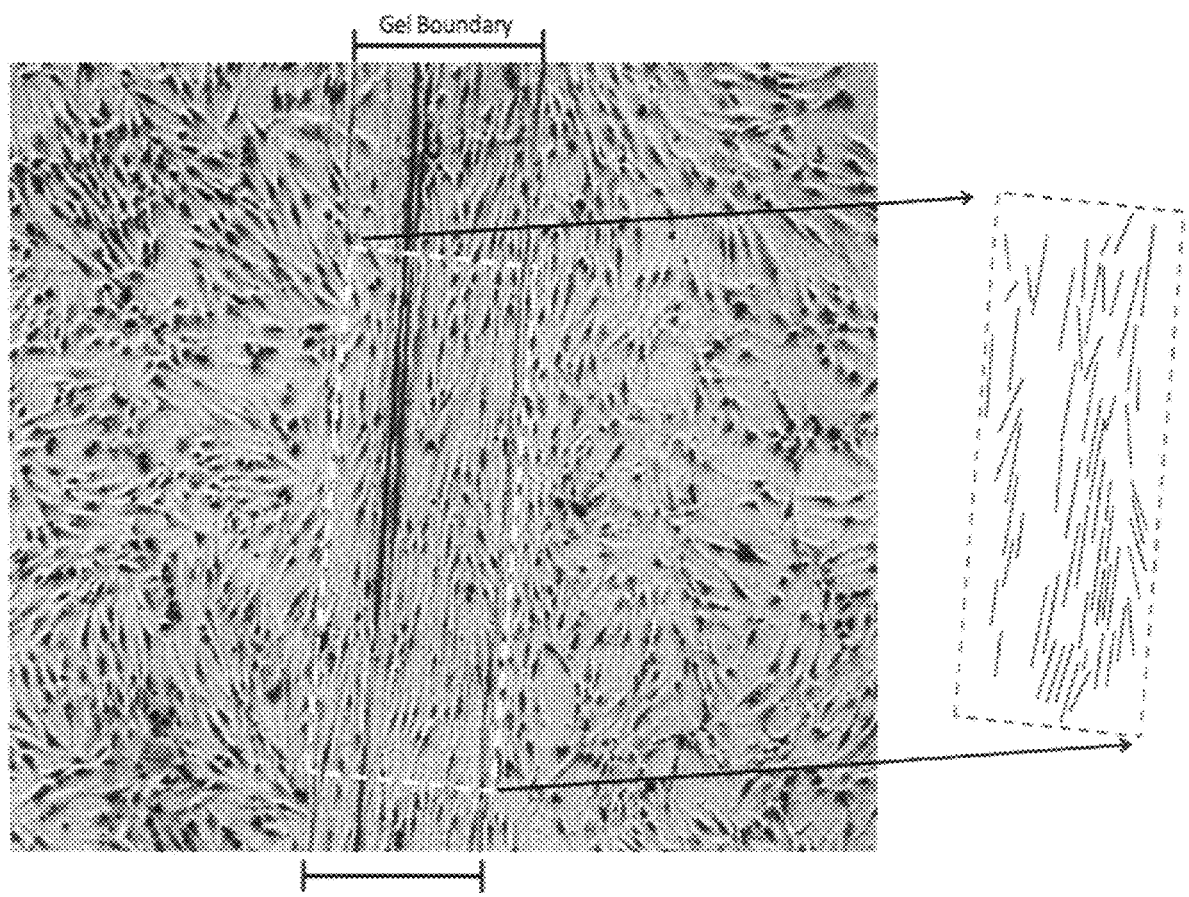
FIG. 6 shows according to an embodiment of the present invention adult human fibroblasts grown on an oriented collagen gel produced by submersion technique. Isotropic cell growth is observed of the gel boundary while on the gel, contact guidance of fibroblasts polarizes cell growth in the direction of deposition (top to bottom). Schematic illustration of cell growth within section of gel is given representing the direction of each cell with a straight line.

The small contact time of the solution of collagen with glass during the deposition procedure could be an issue with this methodology. One could observe the collagen gel to form when submerged into the buffer solution but then float off the substrate. The difficulty with the attachment of the collagen to the glass substrate in this technique could be fixed by chemically treating the substrate to promote better adhesion. One method to promote better adhesion could be by coating the silica glass with a thin coating of collagen before deposition and creation of the oriented gels. The thin coating of collagen, micrograms, is randomly oriented and does not affect the polarization of the cells. FIG. 6 shows a picture of a collagen gel oriented vertically on a silica glass substrate coated with a thin isotropic layer of collagen. The orientation of cells given for a set length of the gel is shown schematically on the right. Within the bounded region a line was placed over each distinguishable cell following the direction of polarization. The gels produced are too thin for the fibroblasts to migrate into the gel, and it is effectively a two-dimensional oriented substrate for cell culture.

Deposition Under PBS Buffer

This section discussed the use of hydrodynamic flow to influence the formation of collagen fibers by orienting the monomers prior to their entry into a neutral pH buffer. The fluid is deposited under the alkaline environment, inducing fiber formation following the exit from the needle orifice. During the deposition process, the fluid is subjected to two flow profiles, the shear flow of the fluid ejected from the syringe, and the extensional flow of the fluid in contact with the substrate being pulled in the opposite direction.

The gels were highly birefringent when viewed between crossed polarizers in a light microscope. FIGS. 7A-C displays a portion of one such gel between crossed polarizers both with (7B & 7C) and without (7A) a quarter wave plate. The gel was produced using a 8.37 mg/ml solution of collagen deposited on silica glass with a 22 gauge needle. The uniform birefringence of the gel is observed in (7A) where only a polarizer and analyzer are present in the optical train. Addition of the quarter wave plate and subsequent sample rotation is shown in (7B) and (7C).

When the molecular orientation is in plane with the quarter wave plate the gel appears blue, and when rotated 90° it appears yellow. The color of the gel with respect to quarter wave plate, confirms that the molecules are oriented along the long axis of the gel, in the direction of deposition. We observed the birefringence of the gel to persist along its length, beyond the field of view of pictures shown.

Figure 8:
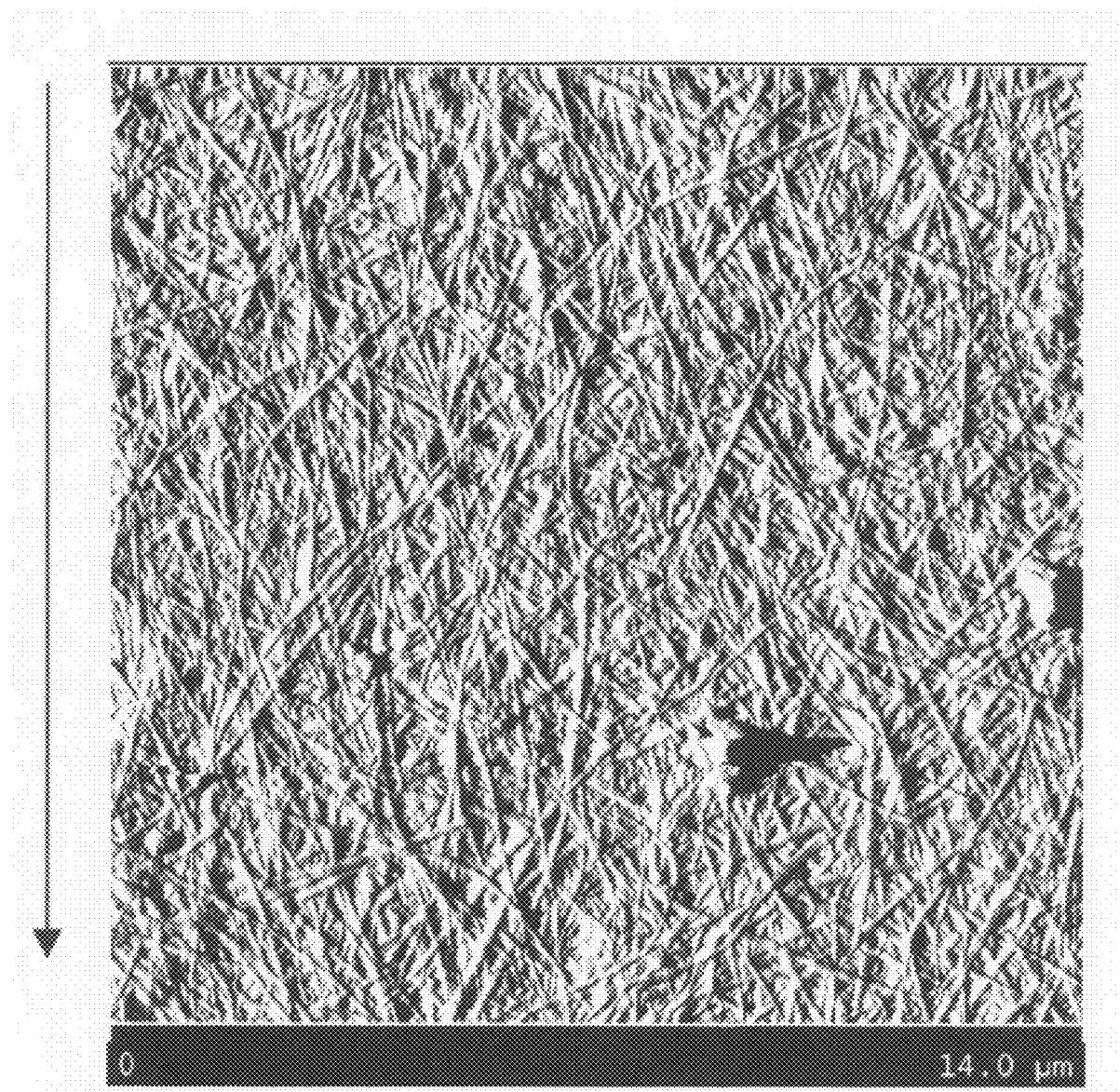
FIG. 8 shows according to an embodiment of the present invention atomic force micrograph of oriented collagen gel in amplitude mode. Arrow denotes direction of flow deposition. (14×14 μm image, 0.6 V scale).

The composition of collagen fibers in the gels was determined by dehydration and observation with the atomic force microscope. Samples were consistent with our previous observations with lengthy collagen fibrils, tens to hundreds of nanometers in width, crossing the image. FIG. 8 displays an amplitude image of a 14 μm section of the gel. The arrow denotes the direction of deposition and a number of fibers are observed to follow this direction.

Figure 9:
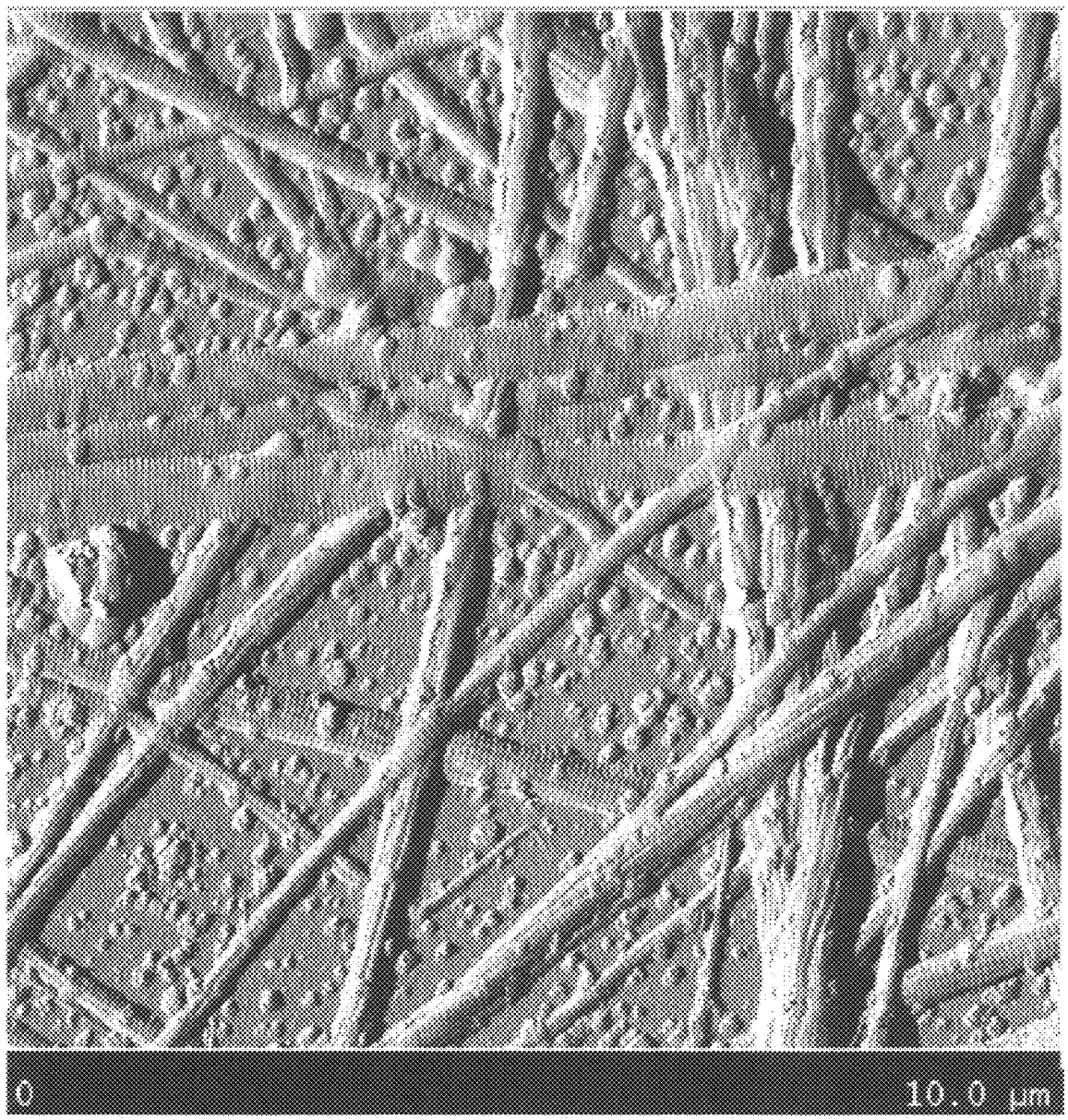
FIG. 9 shows according to an embodiment of the present invention AFM amplitude mode image displaying collagen fibers from the edge of oriented gel. D-Periodicity on collagen fibers is clearly visible. Background of fibers is glass substrate. 10 um×10 um with 0.9 Volt Scale.

A closer view of the collagen fibers of the gel is shown in FIG. 9. The image displays collagen fibers from the edge of a gel on top of the glass substrate. The 67 nm D-periodicity of the collagen fibers is clear, moving across the image from left to right. The diameter range of these fibers is much larger than the image taken from the center of the gel. It is unclear how large the collagen fibers are in the internal portion of the gel and more advanced imaging techniques, such as freeze fracture SEM would need to be utilized.

Growth of Adult Human Fibroblasts

The growth of adult human fibroblasts on the gels provides the clearest picture of the underlying collagen fiber orientation. Collagen fibers naturally provide contact guidance cues to fibroblast cells. The integrin receptors in the cytoskeleton of the fibroblast recognize specific amino acid sequences within the collagen molecule. This recognition produces a cellular response initiating the formation of focal adhesions. These focal adhesions, groups of integrins, are the attachment point between the actin fibers of the cell and the collagen fiber. Upon recognition of the collagen fiber surface, the cell polarizes in the direction of the fiber. The actin fiber network of the cell extends parallel to the fiber allowing the orientation of the fibers to be determined by the direction of the fibroblast growth.

Figure 10:
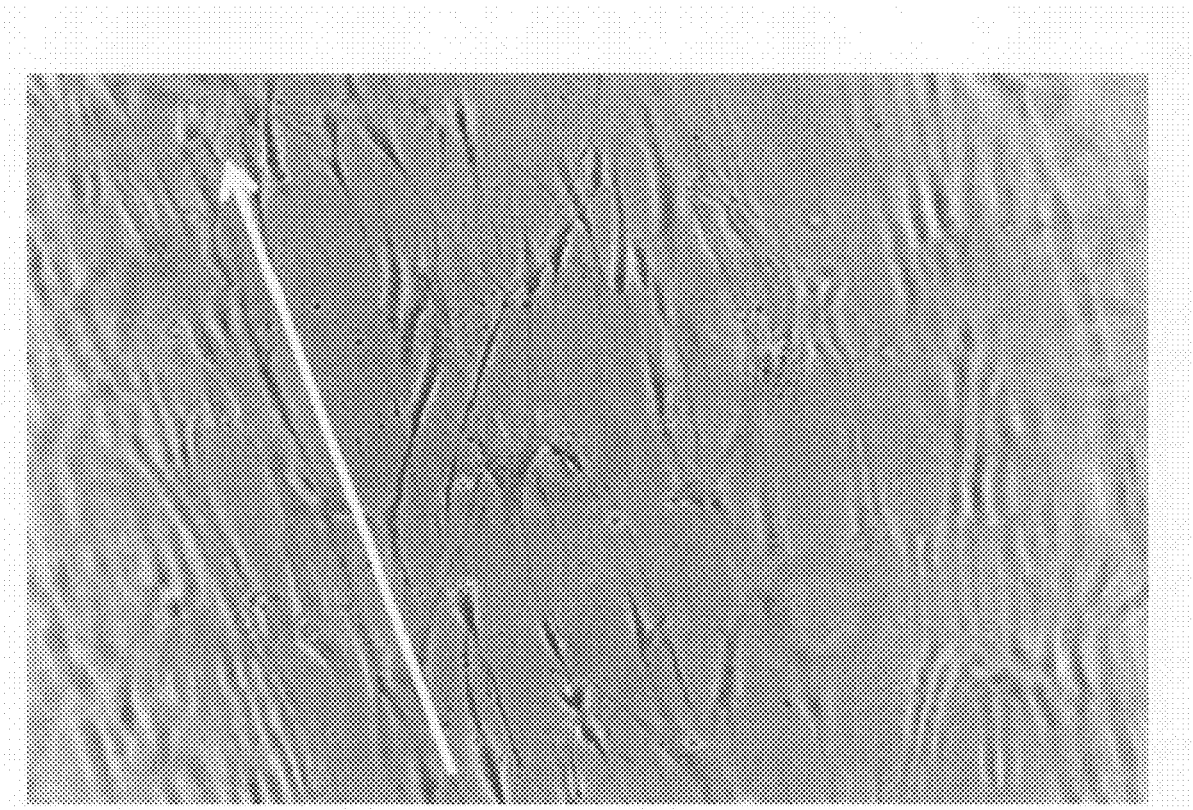
FIG. 10 shows according to an embodiment of the present invention a phase contrast image of adult human fibroblasts grown on collagen gel produced by deposition of highly concentrated collagen solution under 10×PBS buffer. The arrow follows the direction of collagen deposition. Fibroblasts are polarized in the direction of deposition with cellular extensions protruding along this axis. (10× magnification)

In FIG. 10, a phase contrast image of adult human fibroblasts grown on an oriented collagen gel is shown. The fibroblasts were stretched out in the direction of deposition, noted by the arrow. The three-dimensional structure of a collagen gel also provides significant porosity for the cells to migrate internally. While this was not specifically measured it is suggested by the presence of cells on multiple focal planes within the image.

The fibroblasts on the oriented collagen gel are highly polarized with filopodia reaching in both directions along the length of the gel. The cells were grown for 72 hours and then fluorescently stained with phalloidin to illuminate the actin fiber network. Two images are given in FIG. 11 that illustrate the ability of the flow-oriented gels to induce the contact guidance of the fibroblasts. The high population of polarized fibroblasts is representative of a uniform collagen structure guiding the cellular growth.

Figure 11A:
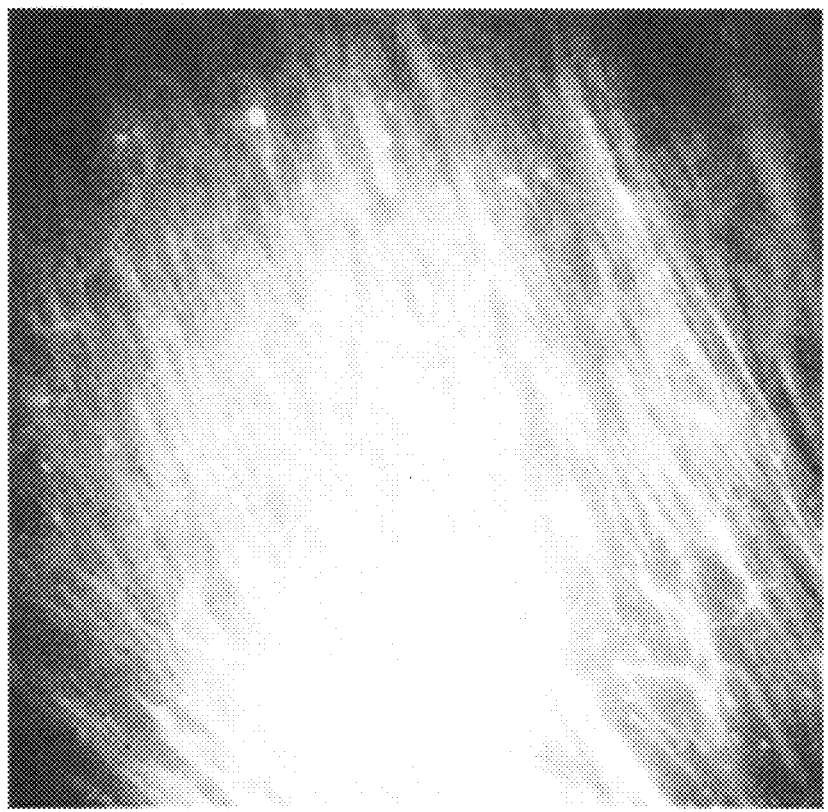
FIGS. 11A-B show according to an embodiment of the present invention fluorescent imaging of cellular actin fiber network. Adult human fibroblast growth on oriented collagen gel created using 10 mg/ml collagen solution in 10×PBS at 37° C. The bodies of the cells are highly polarized in the direction of deposition. (10× (FIG. 11A) and 40× (FIG. 11B) magnification).
Figure 11B:
Figure 12:
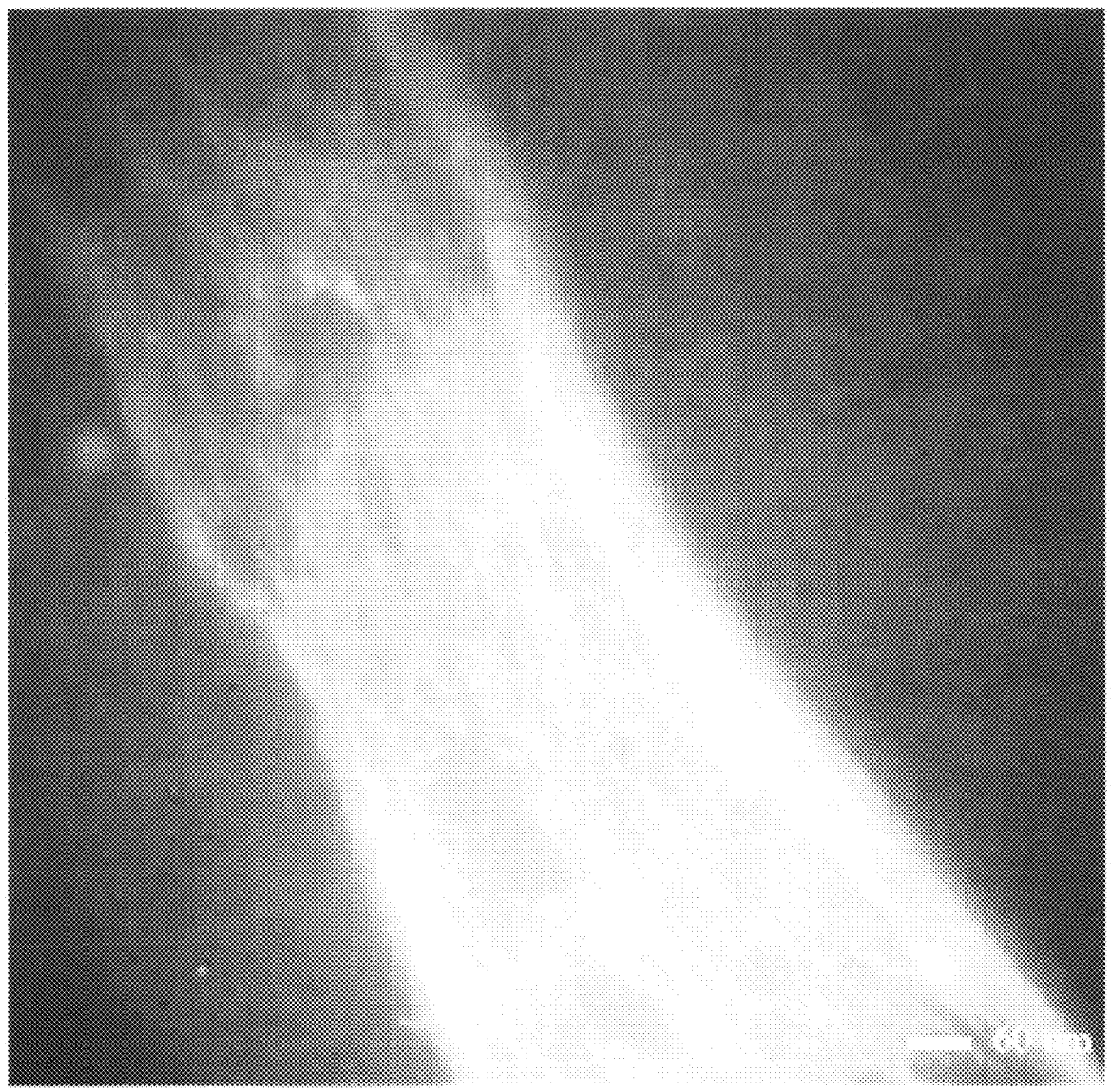
FIG. 12 shows according to an embodiment of the present invention an image of full width of an oriented collagen gel. Gel was produced using a 28 gauge syringe needle and the aligned actin fibers of fibroblasts are visible in the picture. (10× Magnification)

The method described herein is capable of producing oriented collagen gels in a range of sizes. We report here the creation of gels that are hundreds of microns in thickness and tens of millimeters in length. However, it was determined that oriented gels could be produced using both large and small diameter syringe needles. In FIG. 11, a 20 gauge needle was used to create the gel while FIG. 12 displays a much smaller gel, ~500 microns across, created with a 28 gauge needle. In each case, the fibroblasts within the gel are highly oriented, the actin fibers from each cell extending in the same direction, the direction of flow.

We also report the ability to create highly birefringent gels by depositing solutions of collagen ranging from 3.6 mg/mL to ~20 mg/mL. Unfortunately, the manual deposition technique does not provide an accurate measure of the draw ratio of the fluid. We did not specifically compare the attributes of gels produced at different concentrations. Our interest was in the ability to capture the flow orientation. The manufacture of collagen gels using different molecular concentrations will result in different gel porosity and mechanical strength.

Collagen gels produced without a substrate were dispensed directly into the buffer phase and observed to float freely at the air interface. After deposition, they were attached to a glass substrate by bringing the substrate up from the fluid phase and pinning the gel on glass. Some of the gels produced without a substrate did not exhibit uniform birefringence, which is likely related to the lack of extension in the flow deposition process. We have shown herein that the extensional flow component applied to the solution as it is deposited contributes significantly to the ordering of collagen fibrils. Without the constraint of a substrate only the shearing flow of the fluid ejected from the nozzle is present. A promising observation was that these initially unoriented gels could be oriented after deposition by mechanically stretching the long axis of the gel. The stretching of the gel was significant to orient the fibrils, and they did not relax back to an unoriented state. Observations of gels prepared in this manner, with post deposition extension, showed high birefringence signals with uniform direction determined by insertion of a quarter wave plate (results not shown).

APPENDIX

Materials

Rat Tail Collagen, Type I (BD Biosciences) was purchased at stock concentrations of 3.6 mg/mL and 10 mg/ml in 0.02 N Acetic Acid (pH~3.5). The 10 mg/mL solution was then dialyzed against polyethylene glycol (Fluka) for 20 minutes at 4 degrees Celsius until the solution reached a final concentration of approximately 20 mg/ml.

The substrate used was silica glass cleaned by sonication (30 minutes) in a 1.5% Deconex 12-PA cleaning solution at 60° C., rinsed with copious amounts of deionized water (Millipore Direct-Q 5), and stored in clean environment. The silica glass was alternately cleaned by plasma treatment using a plasma cleaner (Gala Instrumente, Prep 5) on 50% power for 5 minutes.

Polydimethylsiloxane, PDMS, (Dow Corning Sylgard 184) was prepared by mixing base and curing agent at a 10:1 mass ratio. A thin coating was applied to silica glass substrates and cured at room temperature overnight or in an oven at 75 degrees Celsius.

Controlled Robotic Deposition

Figure 13:
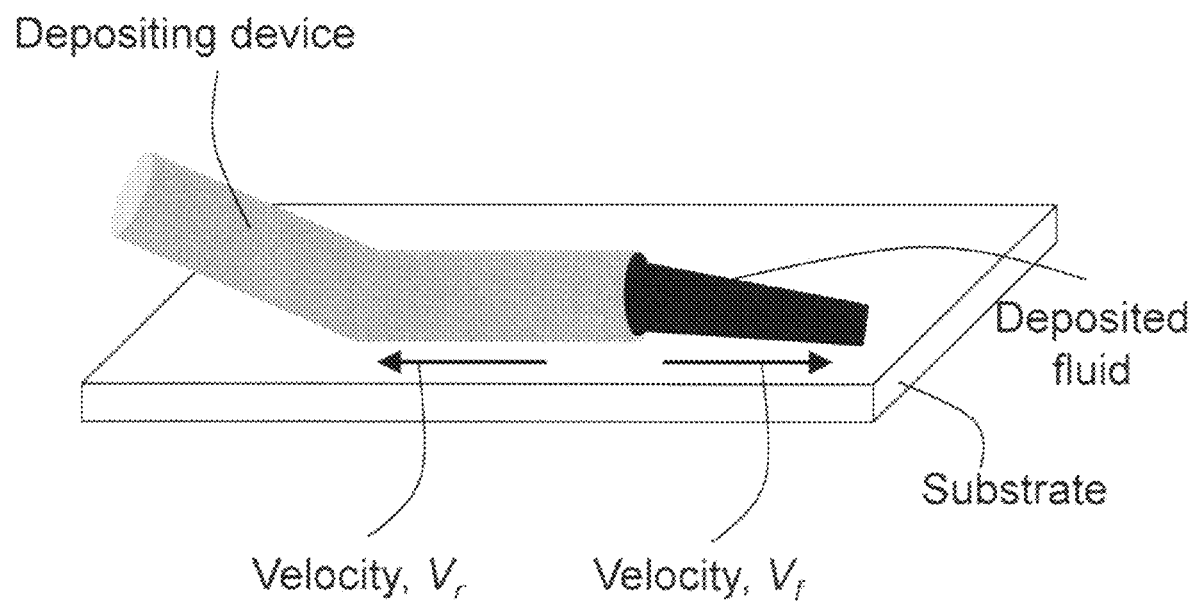
FIG. 13 shows according to an embodiment of the present invention a schematic of robotic deposition onto glass slide. Syringe tip is curved parallel to the glass surface. Fluid exits the orifice with velocity in direction opposite to syringe movement.

Collagen films were created using a custom deposition system that includes a three axis robotic arm (I&J Fisnar 500LN) and a syringe pump (Harvard Apparatus, Milliliter OEM Pump). The design of the apparatus allowed the writing of the collagen solution onto a variety of substrates by programming the robotic arm to follow the path of the surface. The arm of the robot supports a disposable syringe needle connected to an external syringe pump, which dispenses the solutions. The syringe tip is curved so that the exiting fluid is ejected parallel to the target surface, FIG. 13. The opposing directions of fluid and robotic movement creates an extensional flow component in the fluid exiting the syringe. The extensional flow coupled with the pressure driven flow provides significant shear to orient the collagen molecules during deposition.

The flow and deposition were controlled using a custom LabView (National Instruments) program. Fluid deposition was controlled by the draw ratio, the ratio of the substrate velocity to the fluid velocity out of the syringe nozzle, $D=v_r/v_f$. The average velocity of the fluid was calculated from the known volumetric flow rate of the syringe pump, Q, for a given needle orifice radius, R. The average fluid velocity can be calculated from:

$$V_{avg} = \frac{-Q}{\pi R^2} = v_f.$$

The deposition speed of the robot, $v_r$, was adjusted from 20 mm/s to 100 minis. The syringe needle orifice size could also be adjusted by using different needle sizes, 18-27 gauge (inner diameter of 0.84 mm to 0.19 mm). The flow rate of collagen used was in the range of 0.05-0.5 ml/min. The 22-gauge needle was used with the highest frequency and produced the most consistent films for the viscosity of the highly concentrated collagen solutions. A 22-gauge needle at a flow rate of 0.3 ml/min and robot speed of 100 mm/s produces a draw ratio of 2.4.

An example on how to calculate the flow from the syringe needle is as follows. Assume a 22 gauge syringe needle the inner diameter is 0.394 mm (Radius=0.197 mm).

Average Velocity=Flow Rate/Area(0.3 mL/min)/(pi*(0.197 mm^2)).

Flow rate=0.3 mL/min*(1 min/60 sec)*(1 L/1000 mL)*(1 m^3/1000 L)=0.000000005 m^3/sec. Area=(3.14159*(0.000197 meter)^2.

Average velocity=0.041 m/s(41 mm/s). Robot Speed=100 mm/s.

Draw Ratio=(100 mm/s)/(41 mm/s)=2.438.

For a constant Robot Speed of 100 mm/s.
A fluid flow at 0.5 mL/min is a draw ratio of 1.46.
A fluid flow at 0.05 mL/min is a draw ratio of 14.6.

Prior to use, an aliquot of the collagen solution was sonicated at 4 degrees Celsius to reduce the number of collagen aggregates and this procedure has been shown not to destroy the triple helical nature of the molecule. Sonication was done with two, 10 minute pulses of sonication and a 10 minute rest in between. The collagen solution was deposited under controlled flow conditions onto the glass substrates and allowed to dry under ambient conditions. Acidic conditions are maintained in the solution throughout the entire procedure to prevent the formation of fibrils and fibers.

As desiccation of the solution occurs, the concentration of the solution increases while the area of contact remains the same. This rapid volume reduction occurs in less than 15 minutes. The entire apparatus was in a laminar flow hood to maintain sterility for cell culture. After drying, the samples were examined between crossed polarizers on an optical microscope (Nikon TE300).

Cell Growth

Human fibroblasts (ATCC CRL-2091) were cultured on substrates in DMEM media. The media was supplemented with 0.1% FBS, 0.01% 100× penicillin/streptavidin, 0.01% 100× glutamine, 0.01% MEM non-essential amino acids, and 0.01% 100× sodium pyruvate. Cells were plated at a density of approximately 10,000 cells/ml and grown for 12-48 hours at 37° C. with 5% $CO_2$. The cells were fixed in a solution of 10% formaldehyde in 1× phosphate buffered saline (PBS) for 10 minutes. Images were captured with a 10× phase contrast objective using a Nikon TE300 microscope.

Microscopy

Atomic force microscopy was performed on the collagen films using a Veeco Multimode AFM in tapping mode using Nanosensors tips (PPP-BSI) with nominal force constant of 0.1 N/m and resonant frequency of 28 kHz or Tap300A1 tips (Budget Sensors Tap300A1) with nominal force constant of 40 mN/m and resonant frequency of 300 kHz. Scanning was performed at a frequency of 0.5-2 Hz.

For fluorescent imaging of the cellular actin fibers, the cells were stained with Alex Fluor 488 Phalloidin (Invitrogen). The staining protocol is as follows. The growth media is aspirated and the plates are washed one time in PBS and fixed with 3% Formaldyhde in PBS for 10 minutes. The cells are permeabilized with a solution of 1% Triton in PBS for 10 minutes and washed twice with a solution of 0.1% Triton in PBS. Blocking buffer, composed of 5% horse serum and 0.1% Triton in 1×PBS, is then added to the plates for 20 minutes. The fluorescent dye is dispersed in blocking buffer and set on the plates for 1 hour. The plates are washed three times in a 0.1% Triton in PBS solution, mounted with Vectashield (Vector Laboratories) and a glass coverslip, and stored in the dark at −20 degrees Celsius until use. Fluorescent dyes were excited with a Mercury lamp on a Nikon Microphot and Pentamax cooled CCD camera and images recorded with Metamorph Software. Pseudo-coloring of fluorescent images was done using Adobe Photoshop.

What is claimed is:

1. A method of making an oriented collagen gel, comprising the step of depositing with a depositing device a concentration of collagen onto a substrate to induce fibrillogenesis, wherein said depositing device having a depositing speed during said deposition and wherein said concentration of collagen having a travelling speed while being deposited, wherein said depositing speed and travelling speed are both larger than zero, but moving in opposite direction from each other, wherein said depositing step applies both a shear and an extensional force component to said concentration of collagen during said fibrillogenosis, and while said deposited concentration is under a pH buffer of at least 5.

2. The method as set forth in claim 1, wherein said depositing speed is at least 100 mm/s.

3. The method as set forth in claim 1, wherein said travelling speed is at least 0.3 mL/min.

4. The method as set forth in claim 1, wherein the ratio of said depositing speed and said travelling speed is defined as a draw ratio being larger than 0.

5. The method as set forth in claim 1, wherein said concentration of collagen is at least 3 mg/ml.

6. The method as set forth in claim 1, wherein said deposited concentration is under a pH buffer of at least 7.

7. The method as set forth in claim 1, wherein the collagen fibers of said oriented collagen gel have a D-periodicity of 67 nm or about 67 nm.

8. The method as set forth in claim 1, wherein said depositing or the induction of said fibrillogenosis occurs without the application of a magnetic field to said concentration of collagen.

9. The method as set forth in claim 1, wherein said depositing occurs under a physiological temperature.

10. The method as set forth in claim 1, wherein said substrate contains a coating of collagen prior to said depositing step.

11. The method as set forth in claim 1, wherein said oriented collagen gel is used as a drug delivery device or as a tissue engineering system.

12. The method as set forth in claim 1, further comprising pulling or stretching said oriented collagen gel.

13. The method as set forth in claim 1, wherein the ratio of said depositing speed and said travelling speed is defined as a draw ratio is at least 1.

14. The method as set forth in claim 1, wherein the ratio of said depositing speed and said travelling speed is defined as a draw ratio is at least 2.

15. The method as set forth in claim 1, wherein the ratio of said depositing speed and said travelling speed is defined as a draw ratio is at least 3.

16. The method as set forth in claim 1, wherein the ratio of said depositing speed and said travelling speed is defined as a draw ratio is at least 4.

17. The method as set forth in claim 1, wherein said concentration of collagen is at least 5 mg/ml.

18. The method as set forth in claim 1, wherein said concentration of collagen is at least 10 mg/ml.

19. The method as set forth in claim 1, wherein said concentration of collagen is at least 20 mg/ml.

20. The method as set forth in claim 1, wherein said concentration of collagen is at least 40 mg/ml.

* * * * *